United States Patent [19]

Hehli et al.

[11] Patent Number: 5,383,931
[45] Date of Patent: Jan. 24, 1995

[54] RESORBABLE IMPLANTABLE DEVICE FOR THE RECONSTRUCTION OF THE ORBIT OF THE HUMAN SKULL

[75] Inventors: Markus Hehli, Davos-Frauenkirch; Sylwester Gogolewski, Alvaneu-Dorf; Stephan M. Perren, Davos-Dorf, all of Switzerland

[73] Assignee: Synthes (U.S.A.), Paoli, Pa.

[21] Appl. No.: 817,472

[22] Filed: Jan. 3, 1992

[51] Int. Cl.6 .......................... A61F 2/28; A61F 2/30
[52] U.S. Cl. .......................... 623/16; 623/18
[58] Field of Search ................. 623/4, 16, 18

[56] References Cited

U.S. PATENT DOCUMENTS

| | | | |
|---|---|---|---|
| 3,855,638 | 12/1974 | Pilliar | 623/16 |
| 4,186,448 | 2/1980 | Brekke | 623/16 |
| 4,596,574 | 6/1986 | Urist | 623/16 |
| 4,919,672 | 4/1990 | Millar et al. | 623/16 |
| 4,968,317 | 11/1990 | Törmälä et al. | 606/77 |
| 5,084,051 | 1/1992 | Törmälä et al. | 606/77 |
| 5,139,497 | 8/1992 | Tilghman et al. | 623/18 |

Primary Examiner—Randall L. Green
Assistant Examiner—Debra Brittingham
Attorney, Agent, or Firm—Davis Hoxie Faithfull & Hapgood

[57] ABSTRACT

A device for the reconstruction of the orbit of the skull is described. The device is produced from biocompatible polymeric preferably from resorbable polymers having a shape of nonporous and/or microporous plates, membranes or films. The device is preshaped into a three-dimensional element to fit into the orbit of the human skull. Fixation elements with holes being integral part of the device, allow attachment of the device to the skull. Anatomical cuts in the body of the device allow through the nerves and vessels of the eye. An oblong shape of the edges of the anatomical cuts, protects the nerves and vessels from being damaged when the nerves and vessels rub against the edge surface.

18 Claims, 4 Drawing Sheets

RESORBABLE IMPLANTABLE DEVICE FOR THE RECONSTRUCTION OF THE ORBIT OF THE HUMAN SKULL

FIELD OF THE INVENTION

This invention relates to an implantable device for the reconstruction of the orbit of the human skull.

BACKGROUND OF THE INVENTION

High-energy trauma of the mid-face frequently results in bone fracture and a loss of bony fragments within the orbit. It frequently happens, that bony fragments formed upon the fracture cannot be fixed together or are missing and thus, the reconstruction of the orbit is required.

In prior art clinical practice, defects of the orbit, e.g. orbital floor defects are usually treated using metallic, e.g. titanium mesh or nondegradable polymeric implants. The main disadvantage with using nonresorbable implants, however, relates to the necessity of the implant removal from the implantation site, once the healing process is completed. The second operation is traumatic, may lead to secondary infection and increases overall costs of surgical treatment.

The use of a resorbable devices for the reconstruction of the orbit is certainly advantageous, as it avoids second operation. There were several efforts to use resorbable polymers for the treatment of small orbital floor fractures in experimental animals as described by Cutright DE and Hunsuck EE ["The repair of fractures of the orbital floor using biodegradable polylactic acid", Oral Surgery, 33(1), 28(1972)]. In this prior art publication the use of a planar sheet of polylactic acid for the reconstruction of the floor of the orbit is disclosed. The planar sheet is inserted in the orbit, adapted according to the anatomical needs, removed form the orbit and recontoured and finally reinserted into and fixed to the orbit by sutures.

Resorbable devices for treatment of newly created bone voids—a concept which is closely related to Cutright's publication—were disclosed in the U.S. Pat. No. 4,186,448 of BREKKE. In this prior art publication the use of a planar one-piece body of mouldable biodegradable material with randomly shaped interconnected voids therein and having an overall porosity of about 90% is disclosed for the purpose of orbital floor reconstruction.

The main drawbacks of the devices described in these prior art documents relate to their rigidity and limited functionality, in particular to their non-adaptability to the anatomical shape of the orbit. In general therefore, they can only be used for the repair of small defects e.g. in the orbital floor region.

SUMMARY OF THE INVENTION

The present invention avoids these drawbacks, and teaches how to design an implant consisting essentially of a biocompatible polymeric and/or polymeric-ceramic material and being three-dimensionally shapeable allowing the total and/or partial replacement of the orbit of the human skull. The preshaped device can additionally be trimmed at the operation theatres to match precisely the shape of the orbit.

The device according to the invention comprises mainly a flat, flexible element having approximately the shape of the developed curved surface of a frustum of a cone. This special geometrical shape and the flexibility of the polymeric and/or polymeric ceramic material used, renders the device shapeable and trimmable to form a longitudinally slit curved surface of a frustum of a cone for implantation and adaptation into said orbit to be reconstructed. The element is provided with at least one (generally two) indentations at the smaller, top-circle rim of the curved surface which allows for receiving and accommodating the vessels and muscles of the eye.

Preferably resorbable or degradable materials are used for the device according to the invention. Ceramics which can be used for preparation of the device of the present invention are based on e.g. tricalcium phosphate, hydroxyapatite, calcium carbonate and/or their mixtures.

Other materials which can be used for the device according to the invention include mainly polymers such as highly purified polyhydroxyacids, polyamines, polyaminoacids, copolymers of amino acids and glutamic acid, polyorthoesters, polyanhydrides, amides, polydioxanone, polydioxanediones, polyesteramides, polymalic acid, polyesters of diols and oxalic and/or succinic acids, polycaprolactone, copolyoxalates, polycarbonates or poly(glutamicco-leucine). Preferably used polyhydroxyacids comprise polycaprolactone, polylactides in their various chemical configuration [e.g. poly(L-lactide), poly(D-lactide), poly(L/D-lactide), poly(L/DL-lactide)], polyglycolide, copolymers of lactide and glycolide of various compositions, copolymers of said lactides and/or glycolide with other polyesters, copolymers of glycolide and trimethylene carbonate, poly(glycolide-co-trimethylene carbonate), polyhydroxybutyrate, polyhydroxyvalerate, copolymers of hydroxybutyrate and hydroxyvalerate of various compositions.

Further materials to be used as additives are composite systems containing resorbable polymeric matrix and resorbable glasses and ceramics based e.g. on tricalcium phosphate, hydroxyapatite, and/or calcium carbonate admixed to the polymer before processing.

In a preferred embodiment of the device according to the invention the larger, base-circle rim of the curved surface of the base element of the device is provided with perforated tongues and/or straps consisting of the same material as the element for receiving fixation devices, e.g. resorbable bone screws.

In a further preferred embodiment of the invention the device of the invention may be of porous nature, the pore size of the material being in the range of 0.1 to 500 $\mu$m, preferably of 5 to 50 $\mu$m, and the over-all porosity being below 85%.

The rate of resorption and the loss of mechanical properties of the fixation device according to the invention in vivo has to be adapted to allow maintenance of its functionality during the healing period. The rate of resorption can be controlled taking into account that such factors as polymer weight, crystallinity, polymer chain orientation, material purity, the presence of copolymer unit in the chain and presence of voids (porosity) will affect the rate of resorption. In general the rate of resorption increases in the presence of a material with voids, pores, impurities or copolymer units. The rate of degradation decreases with the increase of polymer molecular weight, crystallinity and chain orientation. The polymeric material should preferably have a resorption rate in vivo in the range of 6 weeks to 3 years, preferably between 6 and 12 months, and most preferably between 4 and 7 months.

Viscosity-average molecular weight of polymers to be suitable for preparation of the device according to the invention should be in the range of 15,000 to 1,000,000 and preferably of 150,000 to 400,000, and polydispersity should be in the range of 1.0 to 100 and preferably in the range of 1.1 to 4.5.

The tensile strength at break of the device according to the invention should be in the range of 20 MPa to 5 GPa, and preferably in the range of 50 MPa and 600 MPa.

The device according to the invention may additionally carry bone morphogenetic proteins and/or antibacterial drugs.

The orbit reconstruction device of the invention can be produced from membranes, films or plates by any standard technique used for polymer processing, e.g. compression-moulding, injection-moulding, in-mould polymerization, extrusion, blow-moulding, spraying, vacuum-forming, solution-casting, thermoforming, calandring, etc.

The thickness of plates, membranes or films used for preparation of the device of the invention should be in the range of 0.1 to 3.0 mm, and preferably in the range of 0.2 to 2.0 mm, and ideally in the range 0.5 to 1.5 mm.

Devices of the invention can be produced from oriented and/or nonoriented polymeric material. In the case of oriented materials, orientation can be uniaxial and/or biaxial and preferably biaxial.

The device of the invention may be used in its flat configuration and subsequently (pre- or intraoperatively) be shaped into the desired three-dimensional form. Preferably, however, the device is already pre-bent into a longitudinally slit curved surface of a frustum of a cone which allows maximum adaptability.

The device can be used as a complete construction or only as part of a construction, e.g. a half, three/quarter, etc., depending on the defect in the orbit which should be reconstructed.

The device of the invention will be attached to the bone with resorbable screws, dowels, pins or sutures, and can accommodate bone graft to enhance healing.

The device may be advantageously used for full or partial reconstruction of the orbit damaged as a result of trauma, infection or surgical resection. A further use is as a support for autologous bone graft.

DESCRIPTION OF THE DRAWINGS

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

In the drawings

DETAILED DESCRIPTION OF THE INVENTION

Figure 1:
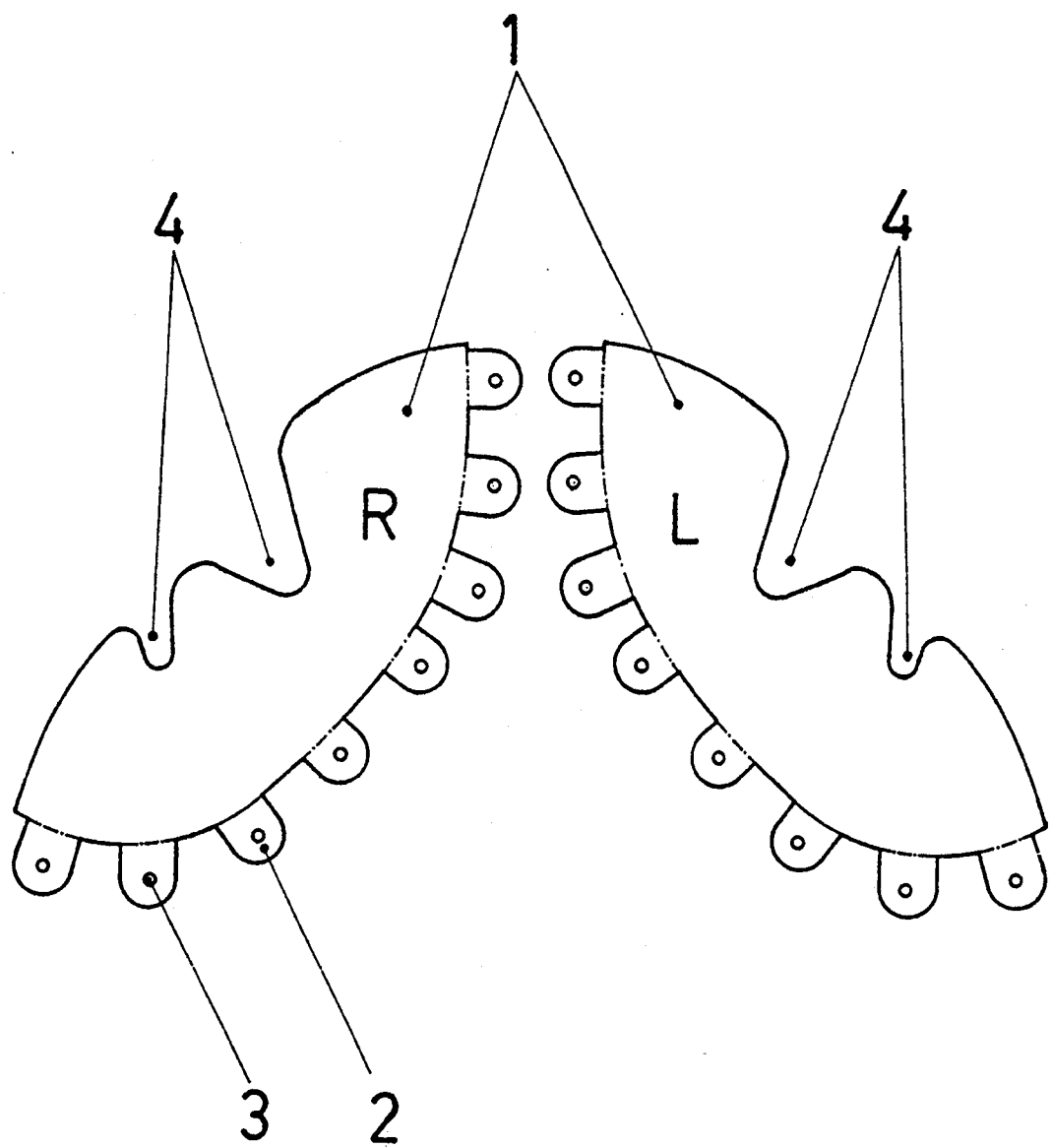
FIG. 1 is a front view of a left-hand and a right-hand embodiment of the invention in the uniplanar form, before it is shaped into the three-dimensional structure.

As represented in FIG. 1 the implantable device for the reconstruction of the orbit of the human skull according to the invention is provided in two mirror-inverted forms R and I, for the right and the left orbit of the human skull. The main body of the device consists of a flat, flexible element 1 having approximately the shape of the developed curved surface of a frustum of a cone.

Figure 2:
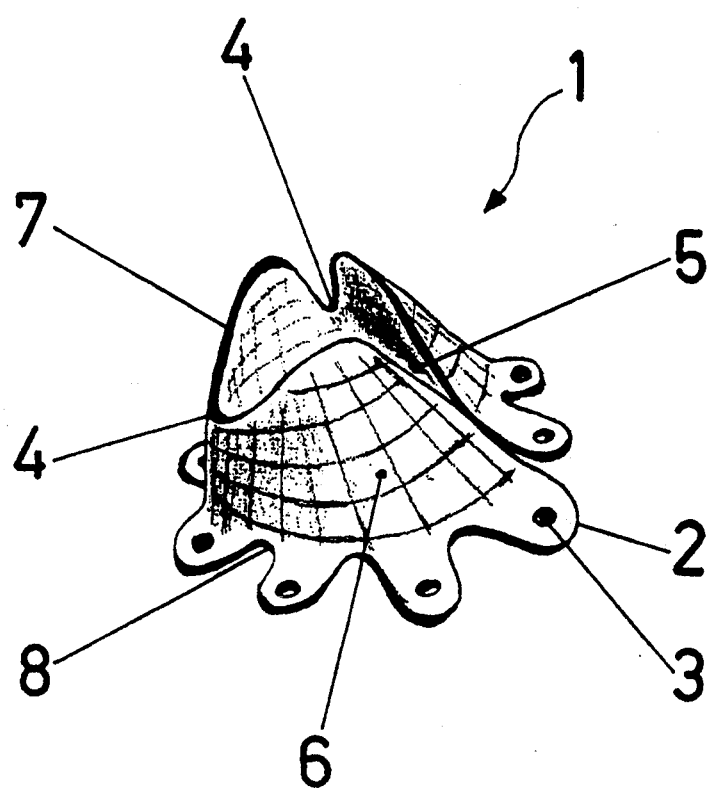
FIG. 2 is a perspective view of the three-dimensionally shaped arrangement of the device according to the invention.

This special form of element 1 allows to shape and trim it preor ]Intra-operatively in a three-dimensional form corresponding approximately to a curved surface 6 of a frustum of a cone having a longitudinal slit 5 as represented in FIG. 2 for implantation and adaptation into the orbit to be reconstructed. The smaller, top-circle rim 7 of the curved surface 6 of element 1 is provided with two indentations 4. These .indentation 4 are anatomically shaped for receiving and accommodating the vessels and muscles of the eye. The indentations 4 have oblong shade to diminish friction between the rims of the element 1 and the vessels and muscles of the eye. The larger, base-circle rim 8 of the curved surface 6 is provided with tongues and/or straps 2 having holes 3 for receiving fixation devices, e.g. resorbable fixation screws.

Figure 3:
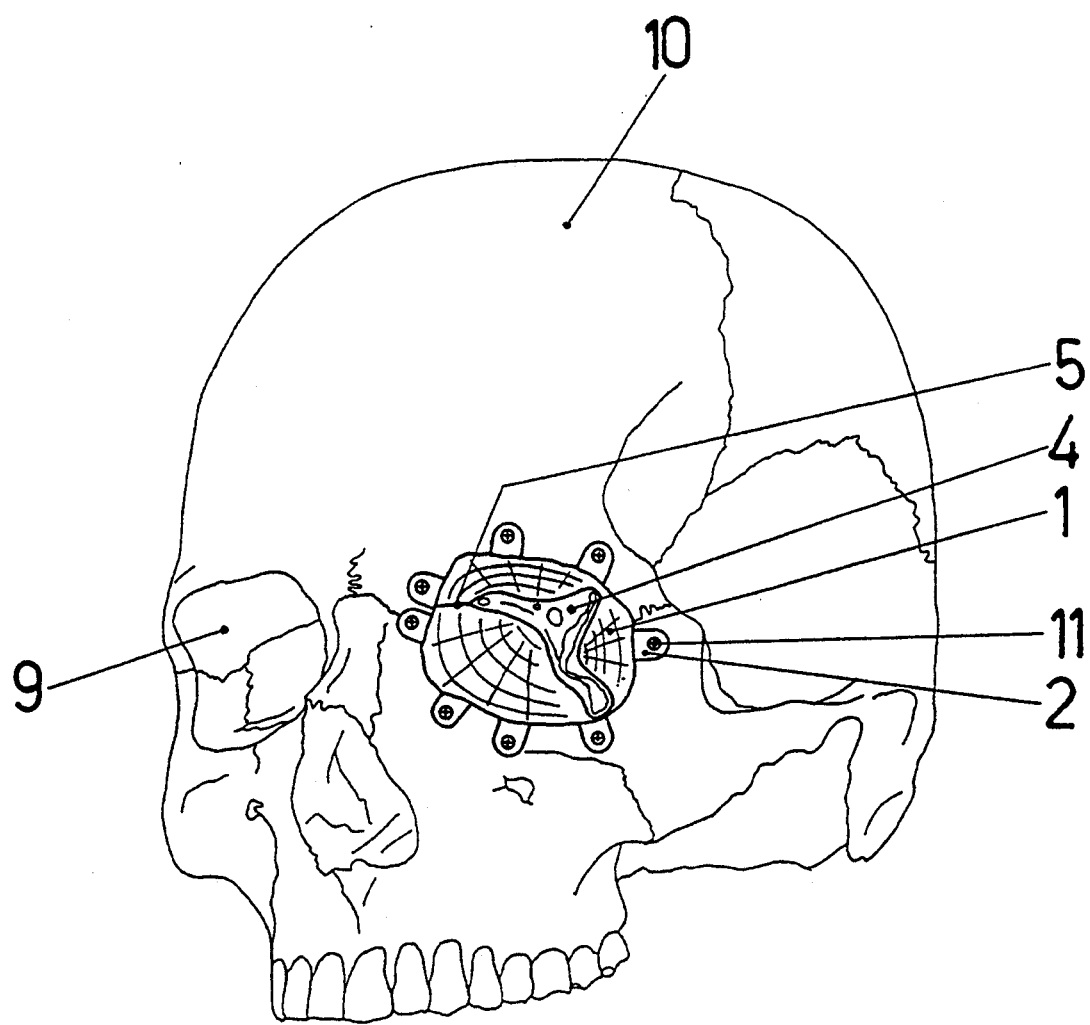
FIG. 3 is a perspective view of the three-dimensional arrangement of the device according to the invention fitted in the orbit human skull.

As shown in FIG. 3 the device according to FIG. 2 may be easily inserted into the orbit 9 of the human skull 10 by adapting the contact area between the lateral edges of element 1 to close the slit 5. Once in place after shaping and trimming to the actual anatomical needs the device according to the invention can be secured to the skull 10 by inserting resorbable screws 11 through the holes 3 of the tongues or straps 2 into the bone.

Figure 4:
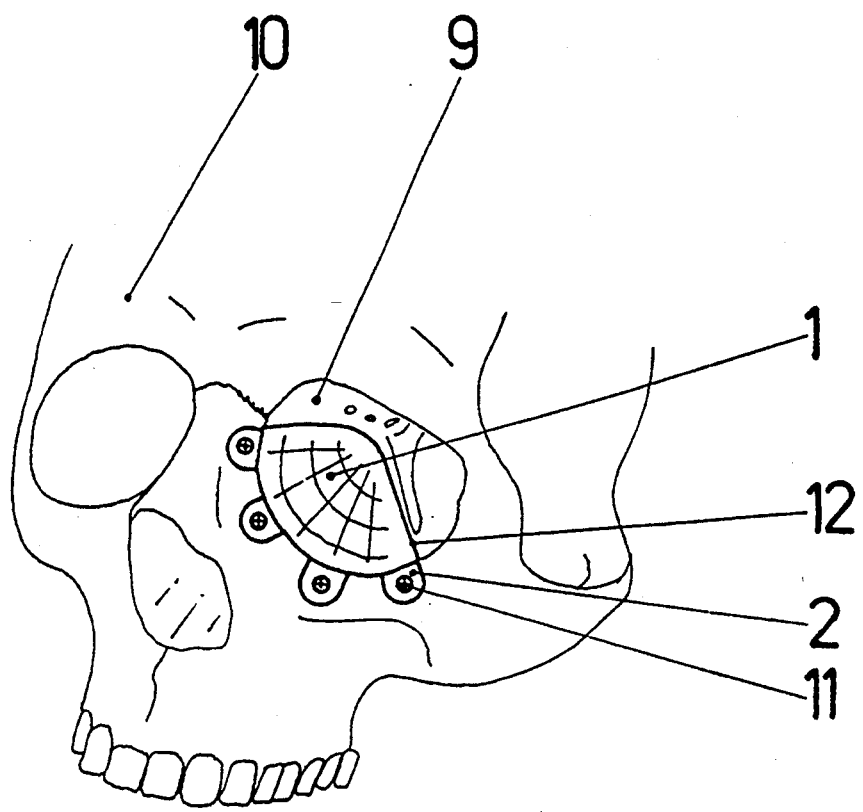
FIG. 4 is a perspective view of the three-dimensional arrangement of the device according to the invention trimmed to the size which is suitable for reconstruction of the orbital floor of the human skull.

FIG. 4 shows how the device according to the invention can be used to reconstruct only part of the orbit 9, namely the orbital floor of the human skull 10. To this effect the element 1 is trimmed along the line 12 in order to produce a suitable artificial orbital floor.

In the following three examples of manufacture of the element 1 are described in detail:

EXAMPLE I

A polymeric non-porous plate with a thickness of 0.5 mm was produced by compression-moulding of poly(L-lactide) with a molecular weight of 400,000 and a polydispersity of 2.6. The plate was produced using a piston-cell apparatus. The element 1 was cut off from the polymeric plate as produced with the aid of a steel cutter, and the holes 3 in the tongues 2 were punctured with a needle. The three-dimensional structure corresponding approximately to a longitudinally slit curved surface 6 of a frustum of a cone was produced by thermoforming to fit the orbit of the human skull.

EXAMPLE II

A uniplanar form of the orbit reconstruction element 1 with a thickness of 1.0 mm and having pores in the range of 5 to 15 μm was produced from poly(L/D-lactide) with a molecular weight of 200,000 and a polydispersity of 3.0 by compression-moulding, using a mould having the desired shape of element 1. The pins installed in the mould and located in cavities for tongues 2, allowed production of the holes 3 in one operation. The three-dimensional structure of the device corresponding approximately to a longitudinally slit curved surface 6 of a frustum of a cone was subsequently produced by thermoforming.

EXAMPLE III

The three-dimensional orbit reconstruction device according to the invention was produced by injection-moulding from poly(L/DL-lactide) 90/10% with a molecular weight of 400,000 and a polydispersity of 2.5. The thickness of the element 1 was 0.5 mm, and the thickness of the tongues 2 was 1.5 mm to enhance stability of the device fixation to the bone. The devices were packed in the pouches and sterilized with ethylene oxide. After evacuation of the devices under vacuum at 35° C., they were used for reconstruction of the orbit in monkeys.

We claim:

1. An implantable device for reconstructing an orbit of a human skull comprising:
   a. a flat flexible element having a shape which is approximately the shape of a developed curved surface of a frustum of a cone, said surface having a circularly curved bottom rim and a smaller circularly curved top rim;
   b. said element having an indentation in the top rim adapted to receive eye vessels and muscles;
   c. said element being made of a material selected from the group consisting of a biocompatible polymeric material and a biocompatible polymeric-ceramic material; and
   d. said element being three dimensionally shapable and trimmable to form a longitudinally slit curved surface for implantation and adaptation into the skull orbit to be reconstructed.

2. A device according to claim 1 in which said material is resorbable.

3. A device according to claim 2 in which said material is a polylactide.

4. A device according to claim 4 in which said bottom rim is provided with straps of the same material as said element having holes for receiving fixation devices.

5. A device according to claim 1 in which said material has pores in a size range of 0.1 to 500 $\mu$m, and a porosity below 85%.

6. A device according to claim 5 in which the pore size is 5 to 50 $\mu$m.

7. A device according to claim 1 in which said material has:
   a molecular weight in a range of 15,000 to 1,000,000 and;
   a polydispersity in a range of 1.0 to 100 .

8. A device according to claim 1 having a tensile strength at break of 20 MPa to 5 GPa.

9. A device according to claim 1 in which said element has a thickness of 0.1 to 3.0 mm.

10. A device according to claim 11 in which said material carries bone morphogenetic protein.

11. A device according to claim 1 in which said material is degradable.

12. A device according to claim 11 in which said material has a molecular weight of 150,000 to 400,000 and a polydispersity 1.1 to 4.5.

13. A device according to claim 1, wherein said material has a resorption rate of at least four months.

14. A device of claim 1, wherein said material has a resorption rate of at least 7 months.

15. A device according to claim 1 having a tensile strength at break of 50 MPa to 600 MPa.

16. A device according to claim 1 in which the element has a thickness of 0.2 to 2.0 mm.

17. A device according to claim 1 in which said material is selected from the group consisting of non-oriented polymers, oriented polymers having uniaxial orientation and oriented polymers having biaxial orientation.

18. A device according to claim 1 in which said material carries antibacterial drugs.

* * * * *

UNITED STATES PATENT AND TRADEMARK OFFICE
CERTIFICATE OF CORRECTION

PATENT NO. : 5,383,931
DATED : January 24, 1995
INVENTOR(S) : Markus Hehli et al.

It is certified that error appears in the above-indentified patent and that said Letters Patent is hereby corrected as shown below:

| | | |
|---|---|---|
| In the Abstract, | line 3, | after "polymeric", insert --materials,--. |
| In the Abstract, | line 6, | after "three-dimensional", insert --structural--. |
| In the Abstract, | line 10, | after "allow", insert --for passing--. |
| Col. 2, | line 19, | before "amides", insert --poly---. |
| Col. 3, | line 18, | delete "spraying". |
| Col. 3, | line 19, | after "solution-casting", insert --spraying--. |
| Col. 3, | line 66, | after "orbit", insert --of a--. |
| Col. 4, | line 9, | cancel "I" and substitute --L--. |
| Col. 4, | line 15, | after "it", cancel "preor]" and substitute --pre- or--; cancel "Intra-operatively" and substitute --intra-operatively--. |

UNITED STATES PATENT AND TRADEMARK OFFICE
CERTIFICATE OF CORRECTION

PATENT NO. : 5,383,931
DATED : January 24, 1995
INVENTOR(S) : Markus Hehli et al It is certified that error appears in the above-indentified patent and that said Letters Patent is hereby corrected as shown below:

Col. 4, line 24, cancel "shade" and substitute --shape--.

Col. 6, line 1 (claim 4) cancel "claim 4" and substitute --claim 1--.

Col. 6, line 27, (claim 14) cancel "of" and substitute --according to--.

Signed and Sealed this

Eighteenth Day of July, 1995

Attest:

BRUCE LEHMAN

*Attesting Officer*     *Commissioner of Patents and Trademarks*